United States Patent [19]
Puderbaugh et al.

[11] Patent Number: 6,026,807
[45] Date of Patent: Feb. 22, 2000

[54] METERED DOSE INHALER CLOUD CHAMBER

[75] Inventors: George Puderbaugh, Manlius; Fredrick M. Richards, Clinton; Lawrence A. Weinstein, Oneida; Deborah A. Laun, Syracuse; David T. Middleton, Jr., Skaneateles, all of N.Y.

[73] Assignee: Diemolding Corporation, Canastota, N.Y.

[21] Appl. No.: 09/031,867

[22] Filed: Feb. 27, 1998

[51] Int. Cl.[7] .................................................. A61M 11/00
[52] U.S. Cl. .................. 128/200.23; 128/200.14
[58] Field of Search ..................... 128/200.14, 200.22, 128/200.23, 202.28, 202.29, 203.11, 205.24, 203.15, 203.12

[56] References Cited

U.S. PATENT DOCUMENTS

| | | |
|---|---|---|
| 2,890,697 | 6/1959 | Van Sickle . |
| 3,209,751 | 10/1965 | Wakeman . |
| 3,994,421 | 11/1976 | Hansen . |
| 4,509,515 | 4/1985 | Altounyan et al. . |
| 4,637,528 | 1/1987 | Wachinski et al. . |
| 4,641,644 | 2/1987 | Andersson et al. . |
| 4,969,578 | 11/1990 | Gander et al. . |
| 5,042,467 | 8/1991 | Foley .................... 128/200.23 |
| 5,103,854 | 4/1992 | Bailey et al. .................... 137/102 |
| 5,385,140 | 1/1995 | Smith .................... 128/200.23 |
| 5,505,194 | 4/1996 | Adjei et al. . |
| 5,855,202 | 1/1999 | Andrade .................... 128/200.14 |

Primary Examiner—John G. Weiss
Assistant Examiner—Charles W. Anderson
Attorney, Agent, or Firm—August E. Roehrig, Jr.; Hancock & Estabrook, LLP

[57] ABSTRACT

A cloud chamber for use with a source of pressurized medication in a MDI system wherein the cloud chamber has a unique one-way inspiratory air and one-way expiratory air valving system which utilizes the same valve body to provide both functions through utilization of different parts of the same valve body for performing the different and mutually exclusive functions. The present invention also provides for the storage of the pressurized medication container within the cloud chamber so that the medication can be conveniently and safely stored when the device in not in use.

8 Claims, 5 Drawing Sheets

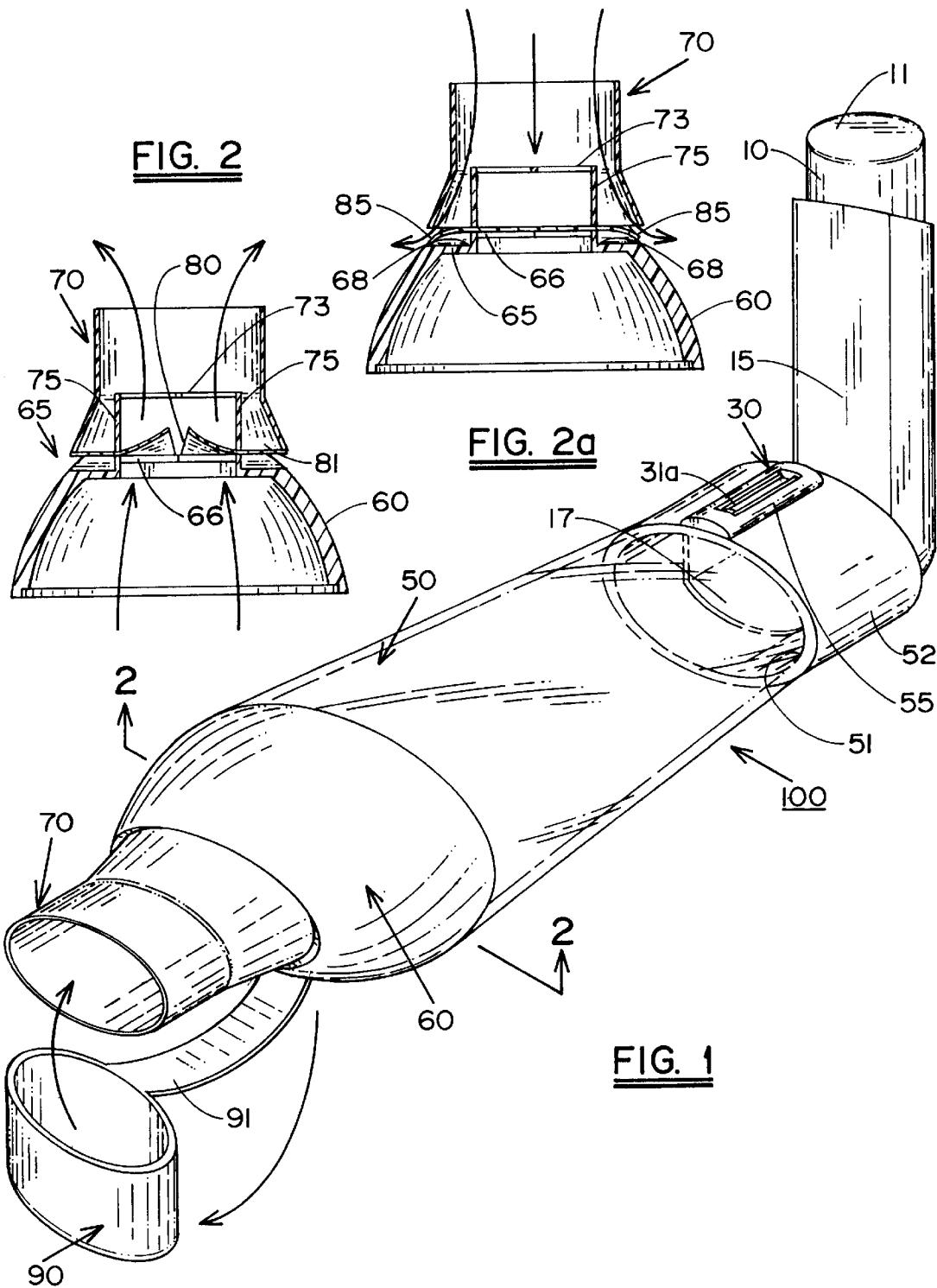

METERED DOSE INHALER CLOUD CHAMBER

NOTICE OF COYPRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by any one of the patent disclosure, as it appears in the Patent and Trademark Office patent files or records, but otherwise reserves all copyright and trade dress rights whatsoever.

BACKGROUND OF THE INVENTION

1. Field of the Invention

This invention relates in general to metered dose inhaler cloud chambers or spacers and, in particular, to a metered dose inhaler cloud chamber having an improved valve system and being capable of storing a pressurized medication dispenser within the spacer or cloud chamber when the medication dispenser is not in use.

More specifically, but without restriction to the particular embodiment and/or use which is shown and described herein for purposes of illustration, this invention relates to an improved cloud chamber for use with a metered dose inhaler, the cloud chamber having a one-way inspiratory air valve and one-way expiratory air valves utilizing the same elastomeric valve body, and which is capable of storing a pressurized medication dispenser, with which the cloud chamber is used, within the cloud chamber when the device is not in use.

2. Description of Related Art

As is known to those skilled in the art, cloud chambers have been used with pressurized medication dispensers for the treatment of persons having respiratory system problems responsive to inhalation therapy. Such devices, referred to as metered dose inhalers (MDI), are used for self-administered inhalation therapy wherein a metered dose of medication is dispensed from a pressurized medication dispenser in the form of a spray or mist which is directed for dispensing into a user's mouth for inhalation into the user's respiratory system.

The pressurized dispensing of such medication directly into a user's or patient's mouth has some objectionable drawbacks, including the uneven distribution of the sprayed medication which condenses on the tongue and inside the mouth rather than being applied to the respiratory system. The condensing of the medication on the tongue creates an objectionable taste, and can cause atrophy of the tongue over prolonged periods of use. Medication which condenses in such a manner on the tongue or inside the mouth is not utilized in the manner intended by the health care professional, and is in effect wasted.

In order to overcome such problems, it has been found that discharging the pressurized medication into a cloud chamber provides a much more effective and efficient means for distributing the medication into the respiratory system as intended. Breathing the mixture of medication and air drawn from the cloud chamber permits more of the medication to reach those portions of the user's respiratory system where the medication is intended to be applied, and is more effective in respiratory care treatment.

When using an MDI with a cloud chamber, it has been found to be preferable for the user to take repeated breaths through the cloud chamber to insure that all of the medication has been utilized in the manner intended. To this end it is preferable that the user not remove the cloud chamber from the mouth once inhalation therapy has begun. Accordingly, it is preferable that some provision be made for drawing inspiratory air in through the cloud chamber, and discharging expiratory air outside of the cloud chamber without removing the device from the user's mouth. Such a provision eliminates the necessity of a user coordinating the dispensing of the pressurized medication with inhalation of the inspiratory air. Also, in this manner the discharge of expiratory air outside of the cloud chamber, prevents the expiratory air, which contains higher levels of carbon dioxide and is normally laden with water vapor, from being re-breathed which would raise the carbon dioxide level and lower the oxygen levels of the user. In addition, if expiratory air is discharged into the cloud chamber, the medication will be blown back out of the device, and the high levels of water vapor from exhaled air will condense in the cloud chamber providing a re-breathing of detrimental bacteria.

The present invention incorporates a unique one-way inspiratory air and one-way expiratory air valving system which utilizes the same valve body to provide both functions through utilization of different parts of the same valve body for performing these functions.

The present invention also provides for the storage of the pressurized medication container within the cloud chamber so that the medication can be conveniently stored when the device in not in use. Without such a convenient storage provision, the medication container can become separated from the cloud chamber resulting in "lost" medicine, and the inability to self-administer the respiratory care treatment as scheduled. Furthermore, such a storage provision prevents debris from entering or clogging the pressurized medication dispenser outlet and eliminates the need for a separate cap to cover the open discharge end of the pressurized medication container.

SUMMARY OF THE INVENTION

It is, therefore, an object of this invention to improve metered dose inhalation therapy devices.

Another object of this invention is to improve the inspiratory and expiratory air valving in a cloud chamber used with a pressurized medication dispenser.

A further object of this invention is to incorporate a convenient storage receptacle for a pressurized medication container into a MDI cloud chamber.

Still another object of this invention is to provide a simpler valving system to incorporate one-way valves for inspiratory and expiratory air.

These and other objects are attained in accordance with the present invention wherein there is provided a cloud chamber for use with a source of pressurized medication in a MDI system wherein the cloud chamber has a unique one-way inspiratory air and one-way expiratory air valving system which utilizes the same valve body to provide both functions through utilization of different parts of the same valve body for performing the different and mutually exclusive functions. The present invention also provides for the storage of the pressurized medication container within the cloud chamber so that the medication can be conveniently and safely stored when the device in not in use.

DESCRIPTION OF THE DRAWINGS

Further objects of this invention, together with additional features contributing thereto and advantages accruing therefrom, will be apparent from the following description of a preferred embodiment of the present invention which is shown in the accompanying drawings with like reference numerals indicating corresponding parts throughout and which is to be read in conjunction with the following drawings, wherein:

FIG. 1 is a perspective view of the cloud chamber of this invention with a source of pressurized medication connected thereto;

FIG. 2 is a partial cross-sectional view of the cloud chamber taken along lines 2—2 of FIG. 1 with portions broken away to better illustrate the one-way inspiratory air valve;

FIG. 2a is a partial cross-sectional view of the cloud chamber taken along lines 2—2 of FIG. 1 with portions broken away to better illustrate the one-way expiratory air valves;

Figure 3:
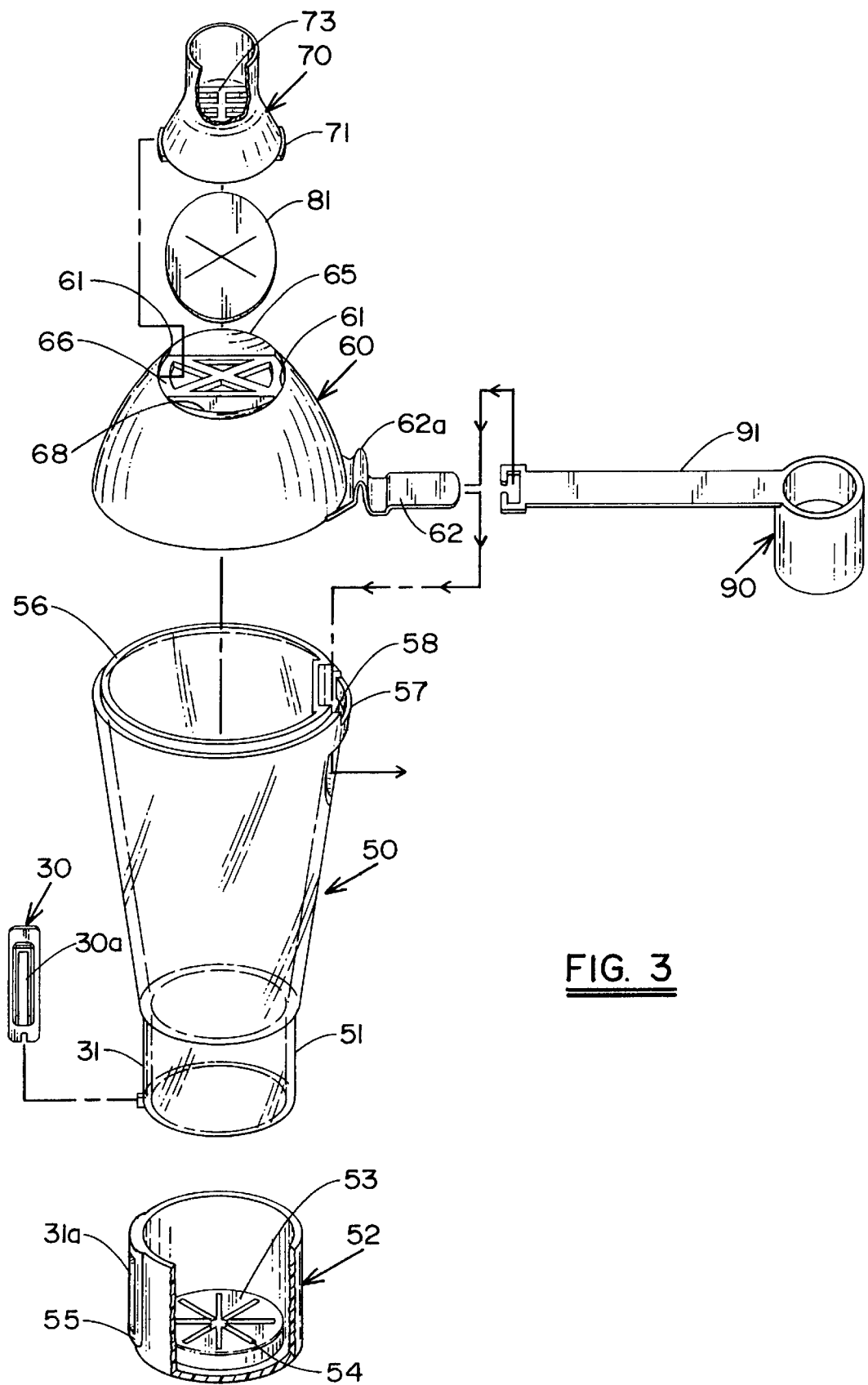
FIG. 3 is an exploded perspective view of the cloud chamber and its components to better illustrate the construction and features thereof.
Figure 4:
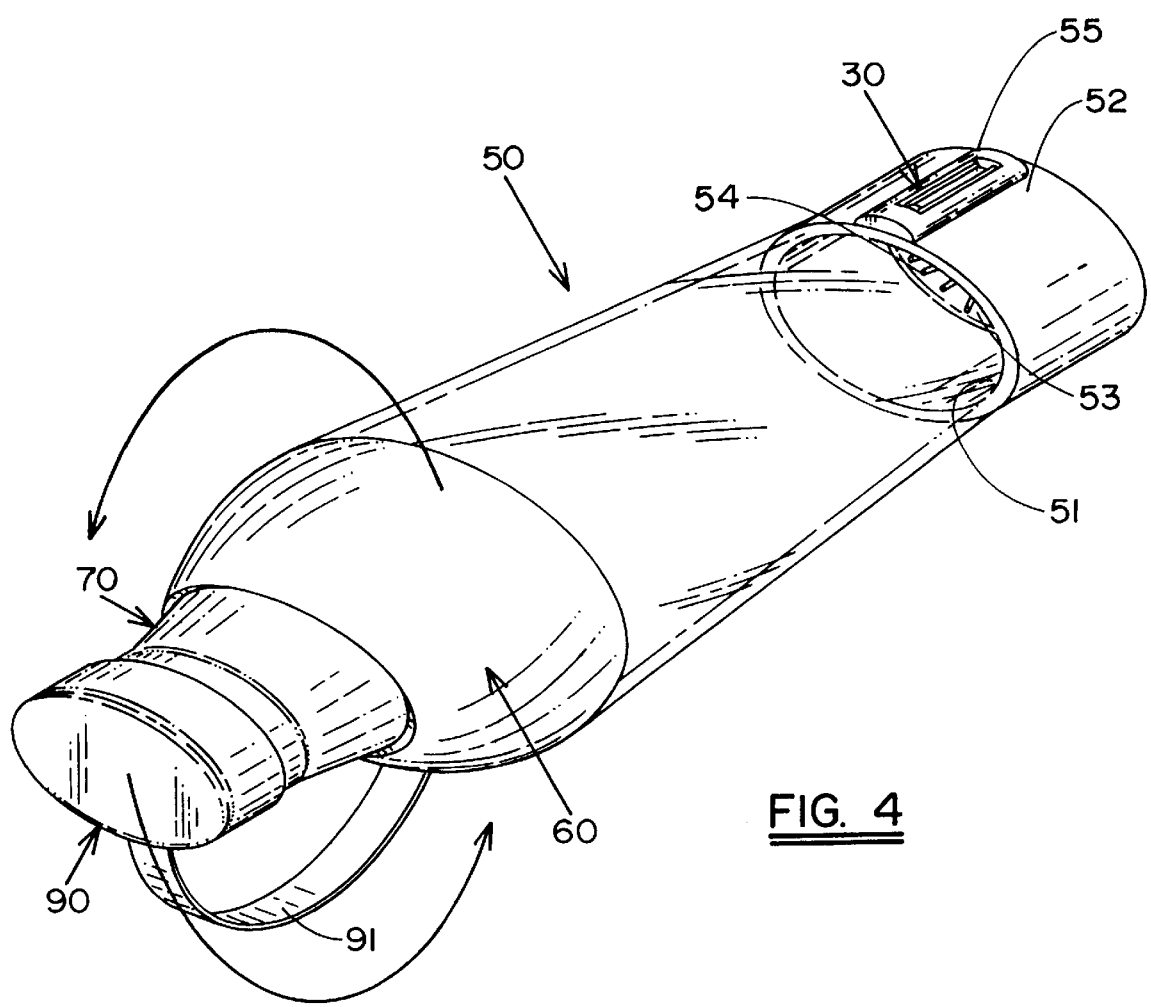
FIG. 4 is a perspective view of the cloud chamber with a mouthpiece cap closing the mouthpiece, and to illustrate the manner in which the cloud chamber opens and closes to receive and remove a pressurized medication dispenser contained therein.
Figure 5:
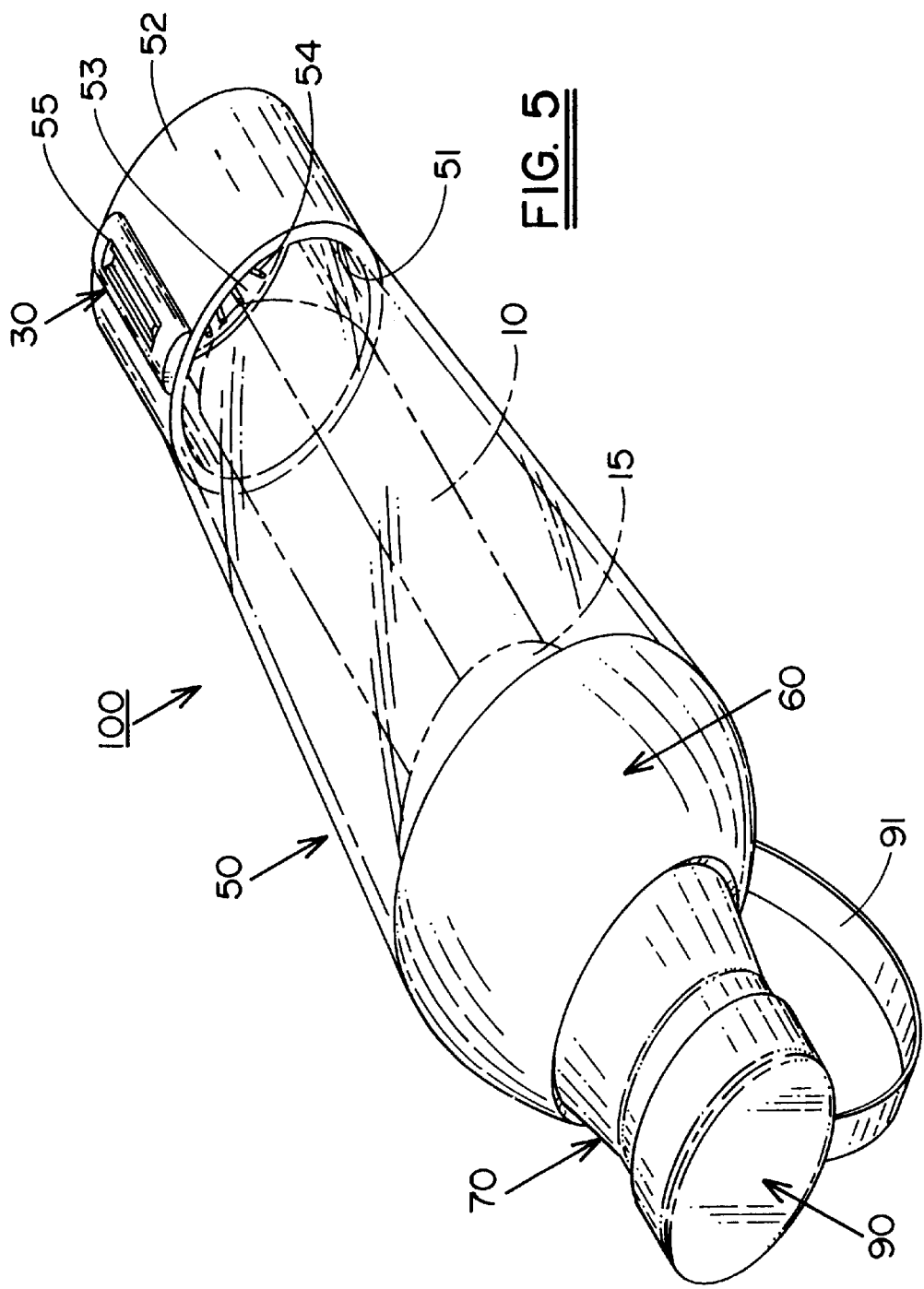
FIG. 5 is a perspective view similar to that of FIG. 4 with a pressurized medication dispenser illustrated in phantom stored within the cloud chamber.
Figure 6:
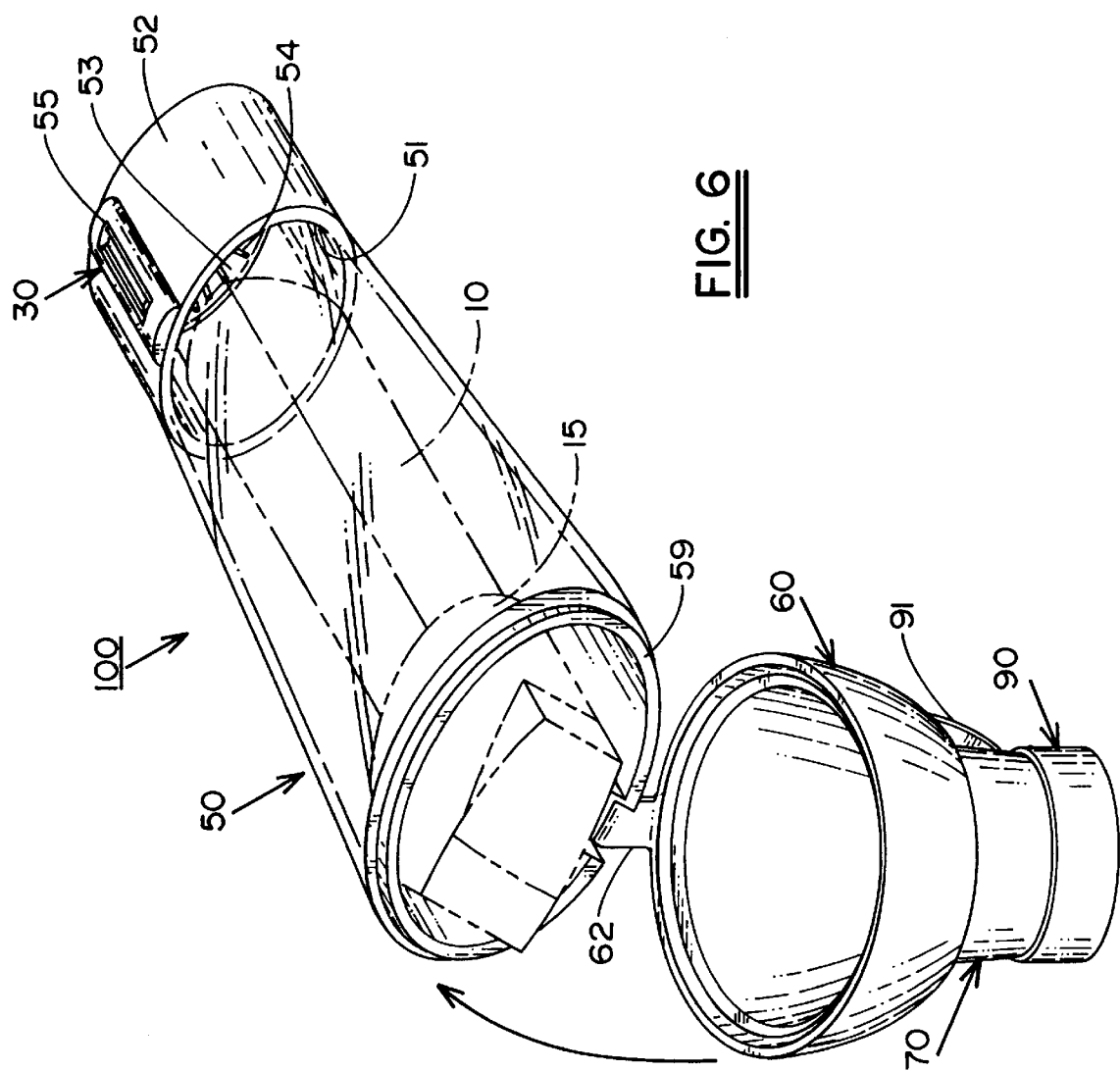
FIG. 6 is a perspective view similar to that of FIG. 5 with the cloud chamber open to illustrate in phantom the pressurized medication dispenser stored within.

These and additional embodiments of the invention may now be better understood by referring to the following detailed description of the invention wherein an illustrated embodiment is described.

DETAILED DESCRIPTION OF THE INVENTION

Throughout this description, the preferred embodiment and examples shown should be considered as exemplars, rather than limitations on the apparatus and methods of the present invention.

Referring now to the drawings, there is shown a cloud chamber or spacer 100 including a source of pressurized medication in a container 10 which is carried in an inverted position by a holder 15 such that downward pressure on an end 11 of the container 10 will cause a spray or mist to be discharged from a discharge outlet 17 through a distal end 51 of a cloud chamber 50. The distal end 51 of the cloud chamber 50 carries a resilient elastomeric or plastic material sleeve 52, a portion of which closes the open distal end 51 of the cloud chamber by means of a plurality of radially extending cuts 54 in the sleeve which extend outwardly from the center to form a plurality of resilient "fingers" 53. In this manner, when a discharge outlet 17 of the container 10 is pushed through the distal end 51 of the cloud chamber 50, the holder 15 will be removably secured to the cloud chamber 50 by the action of the "finger" portions 53 of the sleeve 52 engaging the outer surfaces of the discharge outlet 17.

As best illustrated in FIGS. 1 and 3, the sleeve 52 also secures a signaling device or whistle 30 of the vibrating reed type which is supported in an opening 31 in the distal end of the cloud chamber 50 outside the direct flow of air through the cloud chamber. A raised portion 55 of the sleeve 52, having an opening 31a complementary to the opening 31 in the distal end 51 of the cloud chamber 50, covers the whistle 30 securing the whistle in place in the opening 31. When the MDI is in use, it is important that the user or patient breath in the inspiratory air at a normal rate of inhalation as is customary in such inhalation therapy. To this end the reed 30a is set to vibrate emitting an audio signal to the patient in the event that the rate of inhalation being applied in breathing the expiratory air exceeds a range suitable for normal inhalation. Positioning the signalling device 30 outside of the direct flow of air through the cloud chamber 50 prevents the operation of the signalling device 30 from interfering with the flow and distribution of the medication through the cloud chamber. Such positioning also helps to minimize the diameter of the cloud chamber, and does not interfere with the desired positioning of the pressurized medication dispenser and the intended pressurized discharge of the medication.

The proximal end 56 of the cloud chamber 50 is closed by a chamber cap 60 which is hingedly connected to the cloud chamber 50 by means of a semi-rigid resilient strap 62. The strap 62 extends from the margin of the peripheral edge of the chamber cap 60 and passes between a band 57 and a recess 58 formed in the distal end of the cloud chamber 50. In this manner the strap 62 forms a hinge connection to the cloud chamber 50 about which the chamber cap 60 is swingable in the direction of the arrow shown in FIG. 4, and shown open in FIG. 6, to provide access to the interior of the chamber 50 for storing the medication container 10 and holder 15 when they are not in use.

The chamber cap 60 includes a mouthpiece 70 through which a user withdraws inspiratory air and expels expiratory air. A cover or mouthpiece cap 90 is provided to close the open end of the mouthpiece 70 to keep the mouthpiece clean and to prevent foreign objects from entering. The mouthpiece cap 90 includes a connecting strap 91 which is removeably attachable to a portion 62*a* of the hinge strap 62, best shown in FIG. 3, for connecting the mouthpiece cap 90 to the cloud chamber cap 60 to prevent the mouthpiece cap from being lost. In this manner the mouthpiece cap 90 can be placed over the open end of the mouthpiece 70 in the manner illustrated by the arrows of FIG. 1.

Mouthpiece 70 is secured to the cloud chamber cap 60 by means of tabs 71 engaging slots 61 to which the tabs are heat sealed. A guard grate 73 is carried within the mouthpiece 70 to prevent any foreign objects from passing into a user's mouth when inspiratory air is being withdrawn through the mouthpiece 70. The guard grate 73 is secured within the mouthpiece on a pair of abutment plates 75 which space the guard grate 73 from the adjacent end of the chamber cap 60, and hold the center section of an elliptically-shaped valve body 81 in a fixed position for a purpose to be hereinafter described in detail.

The elliptically-shaped valve body 81 is used to form a one-way inspiratory air valve 80 by the central portion thereof being positioned between the mouthpiece 70 and a proximal end 65 of the chamber cap 60 which is adjacent to the mouthpiece 70, and held against the proximal end 65 of the chamber cap 60 by the abutment plates 75. This one-way inspiratory air valve 80 is formed from the elliptically-shaped valve body 81 of a resilient or elastomeric material having an "X"-shaped cut in the center portion of the elliptical shape, as best seen in FIG. 3. A spider or backing plate 66 is carried at the proximal end 65 of the chamber cap 60 adjacent to one face of the valve body 81 with the cross members of the spider 66 positioned to lie along the "X"-shaped cut to prevent movement of the "X"-shaped cut, or the center portion of the valve body 81, inward toward the cloud chamber 50. In this manner the center section of the elliptically-shaped valve body is fixed between the two abutment plates 75, the spider or backing plate 66, and the distal end 65 of the chamber cap 60.

When inspiratory air is withdrawn through the mouthpiece 70, the "X"-shaped cut in the center portion of the elliptically-shaped valve body 81 will open allowing inspiratory air to be drawn therethrough, as illustrated in FIG. 2. However, when expiratory air pressure is applied against the center section of the elliptically-shaped valve body 81, the "X"-shaped cut in the center portion will be forced against the cross members of the spider or backing plate 66 preventing the "X"-shaped cut from opening and thereby preventing expiratory air from being passed back into the cloud chamber 50, as illustrated in FIG. 2a.

To provide for the discharge of expiratory air through the mouthpiece 70, a portion 68 of the chamber cap 60 adjacent to the outer portions of the elliptically-shaped valve body 81 is undercut. In this manner, as illustrated in FIG. 2a, when expiratory air pressure is applied through the mouthpiece 70, the expiratory air cannot be discharged through the one-way inspiratory air valve 80 for the reason previously discussed, but is applied to the ends of the elliptically-shaped valve body 81 to form a one-way expiratory air discharge valve 85 on both sides of the one-way inspiratory air inlet valve 80 formed by the center section. When expiratory air is discharged through the mouthpiece 70, the ends of the elliptically-shaped valve body 81, which are adjacent to the undercut portions 68 of the chamber cap 60, and therefore are unsupported, function as flapper valves. These portions of the valve body 81 will bend into the undercut portions 68 of the chamber cap 60 allowing expiratory air to pass therethrough and out from the mouthpiece 70, as illustrated in FIG. 2a. In this manner a single piece of elastomeric material 81 forms both a one-way inspiratory air valve 80, and two one-way expiratory air valves 85 while only requiring one valve opening, the "X"-shaped cut in the center portion, to be formed in the valve-forming material.

While this invention has been described in the specification and illustrated in the drawings with reference to a preferred embodiment, the structure of which has been disclosed herein, it will be understood by those skilled in the art to which this invention pertains that various changes may be made, and equivalents may be substituted for elements of the invention without departing from the scope of the claims. Therefore, it is intended that the invention not be limited to the particular embodiment disclosed in the specification and shown in the drawings as the best mode presently known by the inventors for carrying out this invention, nor confined to the details set forth, but that the invention will include all embodiments, modifications and changes as may come within the scope of the following claims:

It is claimed:

1. A cloud chamber for use with a pressurized medication dispenser comprising:

a chamber having an open distal end for receiving therethrough a portion of a pressurized medication dispenser for dispensing a predetermined quantity of medication in a spray or mist form into said chamber, said distal end of said chamber including a retainer carried thereby for forming a closure of said distal end and releasably retaining a pressurized medication dispenser in said distal end, said chamber having an open proximal end for receiving a removable chamber cap forming a closure for the open proximal end of said chamber when received thereon and providing access to the interior of said chamber when removed from the proximal end, a chamber cap for positioning onto said proximal end of said chamber including a mouthpiece through which a user inhales inspiratory air and exhales expiratory air, an air flow control valve positioned between said mouthpiece and said chamber cap for mutually exclusively passing inspiratory and expiratory air as a user inhales and exhales through said mouthpiece, said air valve comprising an ellipse of resilient material having a central flapper valve portion between said mouthpiece and said chamber cap in fluid communication with said chamber, and at least one peripheral portion extending outwardly from between said mouthpiece and said chamber cap forming a peripheral flapper valve in fluid communication between said mouthpiece and an ambient environment, said central flapper valve portion moveable upon the inhalation of inspiratory air by a user from a closed position blocking the flow of expiratory air through said central flapper valve portion into said chamber upon the exhalation of expiratory air by a user and blocking the flow of inspiratory air from said chamber through said central flapper valve portion to the user, to an open position allowing inspiratory air to be inhaled through said chamber, and said peripheral flapper valve moveable upon the exhalation of expiratory air by a user from a closed position blocking the flow of inspiratory air through said peripheral flapper valve into said mouthpiece upon the inhalation of inspiratory air by a user and blocking the flow of expiratory air from said mouthpiece through said peripheral flapper valve into the ambient environment, to an open position allowing expiratory air to be expelled through said peripheral flapper valve into the ambient environment.

2. The cloud chamber of claim 1 further including a vibrating reed signaling device supported in the distal end of said chamber outside a path of air flow from the distal end of said cloud chamber to the proximal end thereof for monitoring a users inspiratory air flow rate.

3. The cloud chamber of claim 1 wherein the open proximal end thereof is of a size sufficient to receive therethrough a pressurized medication dispenser for retaining the dispenser within the cloud chamber when not in use.

4. The cloud chamber of claim 1 wherein said chamber cap is hingedly connected to said chamber.

5. The cloud chamber of claim 1 further including a mouthpiece cap for removably covering an open end of said mouthpiece through which a user inhales and exhales to close the open end of said mouthpiece to keep said mouthpiece clean and to prevent foreign objects from entering.

6. The cloud chamber of claim 5 wherein said mouthpiece cap is hingedly attached to said chamber cap to prevent the mouthpiece cap from being lost.

7. A valve for use with a cloud chamber wherein a pressurized medication dispenser dispenses a predetermined amount of medication into a cloud chamber from where a bolus of medication and air is inhaled by a user, the valve comprising a chamber cover for attachment to a cloud chamber wherein a bolus of air and medication is formed to be inhaled by a user, said chamber cover having a cloud chamber engaging face for receiving a cloud chamber and forming a closure thereof, said chamber cover having a mouthpiece engaging face for receiving a mouthpiece through which a user inhales inspiratory air and exhales expiratory air, said mouthpiece engaging face having an opening formed therein through which inspiratory air can be inhaled by a user, an elliptically-shaped flexible valve body positioned against a portion of said mouthpiece engaging face and across said opening formed in said mouthpiece engaging face, said elliptically-shaped flexible valve body having a central portion having an "X"-shaped cut extending therethrough and of a size corresponding to the diagonal dimension of said opening formed in said mouthpiece engaging face for forming a one-way inspiratory air valve, said mouthpiece opening having an "X"-shaped spider positioned therein forming a backing member for said "X"-shaped cut in said flexible valve body permitting opening movement of said "X"-shaped cut portion toward said mouthpiece when a user is inhaling through said mouthpiece and preventing movement of said "X"-shaped cut portion when a user is exhaling through said mouthpiece, said mouthpiece engaging face having at least one undercut portion adjacent to said mouthpiece opening for receiving a peripheral portion of said emliptically-shaped flexible valve body, said mouthpiece having abutment plates for engaging an opposite side of said elliptically-shaped flexible valve body at a position adjacent to the opening formed in said mouthpiece engaging face for securing said elliptically-shaped flexible valve body between said mouthpiece and said mouthpiece engaging face of said chamber cover, and said elliptically-shaped flexible valve body having a peripheral portion thereof extending outwardly from said central portion forming a one-way expiratory air valve with one face thereof in fluid communication with said mouthpiece and another face thereof adjacent to said undercut portion of said chamber cover permitting opening movement of said expiratory air valve away from said mouthpiece into said undercut portion of said chamber cover when a user is exhaling through said mouthpiece and preventing movement of said expiratory air valve away from said mouthpiece when a user is inhaling through said mouthpiece.

8. The valve of claim 7 wherein said elliptically-shaped flexible valve body has a one-way expiratory valve forming peripheral portion extending outwardly from two sides of said one-way inspiratory air valve forming central portion.

* * * * *